United States Patent [19]

Eschwey et al.

[11] Patent Number: 4,902,559
[45] Date of Patent: Feb. 20, 1990

[54] ABSORBENT BODY OF NONWOVEN MATERIAL AND A METHOD FOR THE PRODUCTION THEREOF

[75] Inventors: Helmut Eschwey, Gorxheimertal; Lothar Hackler, Abtsteinach; Ludwig Hartmann, Weinheim; Michael Kauschke, Waldfischbach-Burgalben; Bernhard Klein, Birkenau-Lo; Thomas Kümpel, Bretten; Hans-Achim Kunkel, Reichelsheim; Torsten Nahe, Mannheim; Ivo Ruzek, Kaiserslautern, all of Fed. Rep. of Germany

[73] Assignee: Firma Carl Freudenberg, Weinheim, Fed. Rep. of Germany

[21] Appl. No.: 192,854

[22] Filed: May 11, 1988

[30] Foreign Application Priority Data

Jun. 16, 1987 [DE] Fed. Rep. of Germany ....... 3720031

[51] Int. Cl.$^4$ .................... A61F 13/16; D04G 1/56; D04G 1/72
[52] U.S. Cl. ................................. 428/224; 156/62.2; 156/62.4; 156/62.6; 428/283

[58] Field of Search ............... 428/283, 224; 156/62.2, 156/62.4, 62.6

[56] References Cited

U.S. PATENT DOCUMENTS

| | | | |
|---|---|---|---|
| 3,449,187 | 6/1969 | Bobkowicz | 156/161 |
| 3,856,012 | 12/1974 | MacDonald et al. | 128/284 |
| 4,198,460 | 4/1980 | Kiss | 428/284 |
| 4,429,001 | 1/1984 | Kolpin et al. | 428/283 |
| 4,755,178 | 7/1988 | Insley et al. | 438/283 |

FOREIGN PATENT DOCUMENTS

| | | |
|---|---|---|
| 0108637 | 5/1984 | European Pat. Off. |
| 0156649 | 10/1985 | European Pat. Off. |
| 0220640 | 5/1987 | European Pat. Off. |

Primary Examiner—Marion C. McCamish
Attorney, Agent, or Firm—Felfe & Lynch

[57] ABSTRACT

Disclosed is an absorbent body of nonwoven material formed of randomly distributed thermoplastic endless filaments which contain embedded hydrophilic or oleophilic staple fibers and in some cases swelling particles. Also disclosed is a one-step process for the production of the absorbent body.

14 Claims, 2 Drawing Sheets

ABSORBENT BODY OF NONWOVEN MATERIAL AND A METHOD FOR THE PRODUCTION THEREOF

BACKGROUND OF THE INVENTION

The present invention is in an absorbent body of nonwoven material with hydrophilic or oleophilic fibers of 1 to 50 mm length, and a method for the production thereof. The absorbent body of the invention has medical, hygenic and technical applications where it is a component of liquid-absorbing products, such as surgical absorbent cloths, products for the absorption of physiological liquids such a diapers, incontinence pads, tampons and sanitary napkins, or highly absorbent wiping cloths as well as automative oil filters.

A layer of shredded, air-deposited cellulose is usually used as hydrophilic absorbent material. The hydrophilic material may be mixed with synthetic fibers.

Known generic absorbent bodies have considerable shortcomings. The absorbed liquid is deposited in the interstices between the loosely laid staple fibers. Under stress, e.g., under the weight or movement of the wearer of a diaper, this liquid easily escapes again as if squeezed from a sponge. Also, due to poor consistency, mats of short cellulose fibers easily fray by creasing and rubbing (wearing of diapers) thereby losing their capillarity and thus their ability to carry the absorbed liquids. Since cellulose fibers are short (1 to 50 mm) and loosely laid to achieve a greater capacity for the absorption of liquid, their capillary function is also inadequate. In other words the transport of liquid into the fiber interstices is imperfect. Consequently far less liquid advances within the absorbent body than the latter would theoretically be able to absorb.

Another drawback of such a product is that its bulk diminishes when it is full of liquid, that is to say that its fluff collapses, its absorption capacity is drastically reduced, and liquid leaks out.

It is possible to increase the capillarity and also the wet strength of an absorbent body by creating a more dense arrangement of the cellulose fibers. This, however, drastically reduces the volume that is available for the absorbed liquid, which is aggravated by the above-described reduction of the absorptive capacity for moisture in the liquid-filled state. If as a remedy the quantity of fiber is multiplied (e.g., several layers of absorbent material), an excessively thick and heavy product is formed, resulting in a considerable increase in material costs and unreasonable handling difficulties. In the case of incontinence inserts, the thickened product is uncomfortable to wear.

There have been many attempts to find a solution to the dilemma of providing absorbent bodies with a high and lasting capacity for absorbing liquids (high bulk, virtually no capillary function) while attempting to increase the distribution of liquid between the fibers via a greater fiber density.

European Patent A 108 637 teaches combining both types of nonwoven material and creating a compressed composite consisting of a thin, highly compressed fiber mat as liquid distributor, plus a loosely laid fiber mat of low density for the storage of the liquid. The dense fiber mat contains hydrophilic fibers and is backed with a lightly compressed fiber layer which contains superabsorbent polymers (swelling bodies, superabsorbers). Such polymers are water-insoluble, hydrophilic polymers which can absorb at least 15 times their weight of water. They are used in the form of powders, flakes or granules.

The light pressing of the superabsorber particles between two layers of fiber, plus, in some cases, fixation with adhesives, binding agents or by embossing, is intended to fix the particles in a uniform distribution to prevent their leakage in the dry state and, to prevent them, in the presence of moisture, from conglomerating due to the lack of sufficient separation thus interfering with the liquid distribution.

The disadvantage of such fixation is that the particles have a very limited amount of space available to swell into. As such, their ability to absorb liquids is considerably impaired.

Furthermore, an absorbent body according to the above patent has good liquid distribution in the high-density fiber layer, yet transport into the actual storage layer is disturbed since there is no direct contact between the transporting layer and the superabsorber particles; the outer surface of the layer fixing these particles acts as a barrier to liquids.

Also, in the wet state the composite easily separates and becomes lumpy.

Composites, finally, are always relatively stiff and inelastic and so they are uncomfortable to wear in incontinence products. Their production requires several separate steps.

SUMMARY OF THE INVENTION

The present invention is an absorbent body of nonwoven material which has a good ability to conduct liquids and a good holding and absorptive capacity. In the interest of wearing comfort (which is important in the case of incontinence products) it is also to have a reduced thickness combined with greater flexibility and stability than is the case with the generic absorbent body composites of the state of the art. Furthermore, for all applications in the hydrophilic or in some applications in the oleophilic areas, the absorbent body is to have good strength both in the dry and wet states. If superabsorber particles are incorporated, they are to be uniformly distributed and fixed in the fiber structure but have sufficient space available for swelling. The unhampered transport from the outer surface of the absorbent body to the swelling substances must be assured.

The invention also includes a process which requires fewer steps than the conventional depositing of layers of different absorbing bodies.

The various features of novelty which characterize the invention are pointed out with particularity in the claims annexed to and forming a part of this specification. For a better understanding of the invention, its operating advantages and speciifc objects obtained by its use, reference should be had to the accompanying drawings and descriptive matter in which there is illustrated and described a preferred embodiment of the invention.

DESCRIPTION OF PREFERRED EMBODIMENT

Figure 1:
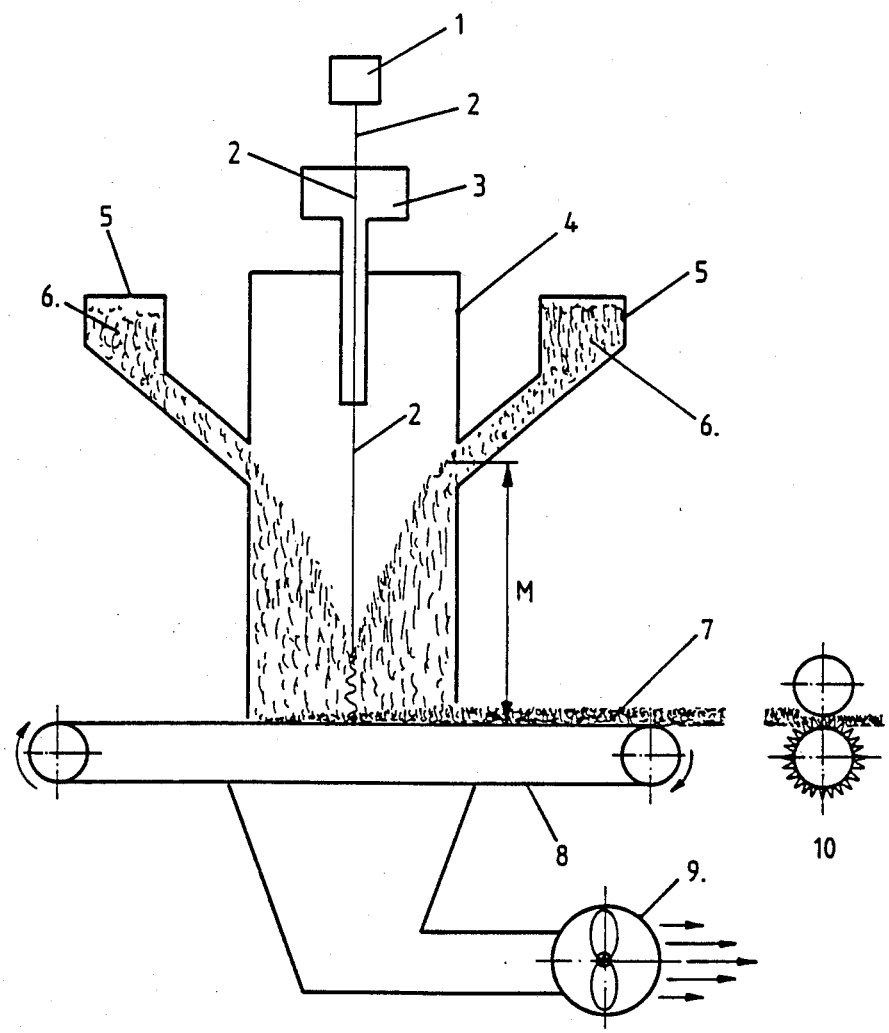
FIG. 1 is a schematic of an arrangement of an apparatus for the practice of the method of the invention.

All of the above discussed requirements, some of which heretofore have been considered contradictory, are satisfied by the invention.

The invention is in an absorbent body of nonwoven material which contains hydrophilic or oleophilic fibers and in which a single-layer network, having a total density of from 0.05 to 0.5 $g/cm^3$, and a matrix of thermoplastic endless filaments of circular cross section and a high degree of orientation, run in a three-dimensional random texture. The hydrophilic or oleophilic fibers are distributed in a spatially uniform manner in an amount of 40 to 90 percent by weight of the total sheet material.

The present invention is also in a manufacturing process in which rows of filaments are spun from a melt by means of one or more spinnerets and are deposited on a horizontal uniformly moving air-permeable support having underneath it an air aspirating apparatus. The endless filaments are spun and the hydrophilic or oleophilc fibers of 1 to 50 mm length are added in a downwardly extending air stream, approximately in the bottom third of the distance between the spinneret and support, in an amount of 40 to 90 weight-percent with respect to the total material weight. The fibers come in contact with the filaments, which are no longer tacky. The movement of the support is so controlled that the endless filaments are deposited in a three-dimensional, uniform random texture without preferred direction, and are mixed uniformly with the hydrophilic or olephilic fibers.

The process further includes the addition of superabsorber material in an amount of 2 to 50 wt.-% of the total deposited material. The superabsorber may be added with the fibers. The process also includes compressing the deposited filaments and fibers with a line pressure of no more than 150 kp/cm under the action of an amount of moisture that is such that it makes the superabsorbent particle surfaces tacky, but without initiating the swelling process.

The absorbent body according to the invention can be used in all of the above-mentioned fields of medicine, hygiene and technology, whenever a highly absorbent, wet-strength, liquid retaining product of minimum thickness is required.

The use according to the invention of endless matrix filaments of circular cross section and a high degree of molecular orientation has led surprisingly to an absorbent body of extremely high strengths.

The high degree of orientation is attained by stretching the filaments and means, that the macromolecules are oriented substantially parallel to the major fiber axis. A measure for this situation is the double refraction: the fibers according to the present invention show a double refraction of 0.020 to 0.032.

An embodiment that is advantageous as regards absorbency is characterized by an additional content of 2 to 50 weight-percent of bodies of highly abosrbent polymer in a spatially uniform distribution. Such "superabsorbers" are, for example, saponified starch-polyacrylic graft polymers, starch-polyacrylate graft polymers, crosslinked or grafted cellulose, sapoinified acrylic acid polymers and saponified acrylic acid copolymers, crosslinked polyethylene oxides, carboxymethylcelluloses, and the like. Absorbent sheet materials containing partially crosslinked polyacrylic acid derivatives of starch graft copolymers have proven advantageous.

It is often possible to employ the absorbent bodies of the invention without further consolidation or compression for one-time use as an absorbent layer, since the endless filaments form in their spatially scattered texture a self-supporting matrix for the hydrophilic and oleophilic components that has wet and dry longitudinal and transverse strength.

One advantageous alternate embodiment consists therefore of a highly compressed absorbent body of unfused endless thermoplastic filaments. Even the unconsolidated absorbent body has an extremely good wet and dry strength. The great compression promotes the distribution of the liquid; the free movability of the matrix filaments promotes the unhampered swelling of the superabsorber.

Another preferred alternate embodiment is one in which the superabsorbent substances adhere to the fibers and surrounding filaments and are thus anchored in the enveloping fiber matrix. The superabosrber particles are able in all of the named instances to easily expand the surrounding fiber structure in the swelling process, so that absorbency for liquids is very high even in a compressed product. The swelling substances also increase the capacity for liquid retention.

The thickness and density of the absorbent body according to the invention are widely adaptable to particular requirements without departing from the scope of the present invention.

The good ability to distribute liquids is surprising. According to the state of the art, one would expect that a homogeneous mixture of superabsorber and hydrophilic fibers would tend to form gel blocks, i.e., that the liquid distribution would be more greatly impaired than in the case of a loosely deposited fluff. Surprisingly, however, it has been found that the embodiment of the absorbent body according to the invention in no way impairs the liquid distribution, which can be explained by the endless filaments present as a framework in the random texture.

A preferred field of application for the absorbent body of the invention is incontinence products for small children and adults, such as throwaway diapers, diaper pants, sanitary napkins and bed pads. These products consist essentially of a bottom layer imperable to liquids (usually film), an upper, moisture-repellent layer permeable to liquids (fiber mat or perforated film) and the absorbent body according to the invention between these layers.

All incontinence products of such a nature have in common a considerable improvement in wearing comfort.

The wet absorbent layer holds together even when the wearer moves about. The fiber structure of the liquid accumulator is not interrupted, liquid does not leak out.

Conglomeration of the wet superabosrber, such as often undesirably occurs, especially in cellulose fiber mats in adult diapers, is prevented. The good strength characteristics in the longitudinal and transverse direction, even without consolidation, also make the absorbent body advantageous for use in tampons and in medical swabs.

The absorbent body of the invention can be used in the technical field in its hydrophilic variant as an absorbent fiber material containing superabsorbers for cable jacketing. Medium- and high-voltage cables contain these absorbent fibers between the jacket and the sheating for the purpose of immediately binding and fixing any water that might enter in case of damage to the cable an at the same time, by immediate, intensive swelling, forming a water-tight plug at the damage site. The requirements are thus the same as in the hygienic products: medium thickness combined with great ability on the part of the particles to swell and expand unhampered.

Due to its outstanding strength, the absorbent body of the invention is highly suitable as the sole component or absorbent component of a wiping cloth. Here again, the desirable properties of the absorbent body according to the invention, such as thinness combined with great absorbency, a high liquid retention capacity, and high inherent strength, even in the soaked state, are highly advantageous.

The absorbent body of the invention can be used as a retainer or absorber for substances containing oil by using oleophilic fibers therein. By this is meant substances which have an affinity for oleophilic materials. Thus, the absorbent body of the invention can be used for the separation of oils from water and air, and in the medical or cosmetic fields.

Such oleophilic fibers, for example, are staple fibers of polyolefins. The use of oleophilized mechanical wood pulp has very recently proven especially advantageous in the separation of oil from water.

It is possible, of course, to mix thermoplastic binding fibers additionally into the absorbent body, if it is exposed to particularly great mechanical stress. The use of a spray binder is also possible.

The process of the invention has the advantage of being of single step process.

Preferred spinnable substances for the production of the endless filaments include polypropylene, polyethylene, polyester, polyamide or polyurethane.

The endless filaments are deposited in a three-dimensional random texture approximately simultaneously with the hydrophilic or oleophilic fibers and the swelling substances, if any, mixed therewith. The deposited web, under which there is an air aspirating system, moves substantially slower than would correspond to the spinning rate of the thermoplastic filaments. A crinkled deposit (three-dimensional scattered texture) is formed, and thus a thermoplastic matrix in which the hydrophilic fibers, plus the superabsorber particles, if used, are enclosed. The absorbent body thus produced can be employed without any further consolidation, especially for one-time use. The powdering out fibers or particles is negligible.

It may, however, be advantageous to compress and consolidate the fiber sheet under pressure and heat. The applied heat must suffice to render the thermoplastic materials in the nonwoven material tacky. A full-surface, linear or spot indentation is performed depending on the desired degree of compression.

If superabsorber particles are present, which may be added in amounts of 2 to 50% of the total weight, it is especially advantageous to perform a full-surface compression of the sheet material in a moist atmosphere at a linear pressure up to a maximum of 150 kp/cm. In the presence of moisture the superabsorbing particles, without swelling, adhere to one another and to the surrounding fiber materials. Thus a consolidation of the structures is achieved, which will be lost again upon the access of liquid and will permit unhampered swelling.

The degree of compression can vary greatly depending on the use to which the absorbent body according to the invention is to be put. If, for example, the absorbent body of the invention is to be used for a wiping cloth, the surface should be more highly consolidated to achieve a higher resistance to chafing. For a wiping cloth a fiber web of 200 g/m$^2$ (area) is consolidated to a density of about 0.2 g/cm$^3$. This can be performed either by calendering with a textured cylinder or also expediently by spraying on a binding agent.

If the absorbent sheet material is to be used as a diaper, the absorbent body should have a greater bulk and the surface consolidation need not be as extensive, because in the manufacture of diapers a covering material generally protects the absorbent layer against chafing wear.

Referring to FIG. 1, one or more rows of endless filaments 2 are spun through a long spinneret 1 which has the same number of rows of orifices. The filaments 2 pass through a guiding and stretching passage 3 where they are stretched to the desired extent by air blasts parallel to their direction of fall. The velocity of the air streams can be up to the velocity of sound. After passing through guiding passage 3, the endless filaments 2 then pass into a shaft 4 the bottom third of which forms a mixing area M. In mixing area M the hydrophilic or oleophilic fibers 6, fed from a grinding mechanism 5, are mixed with filaments 2. Any superabsorber particles which may be added are also introduced in mixing area M. Air streams can also aid in the addition of the fibers and particles, which enter on both sides of the rows of filaments.

The filaments and fibers, plus the superabsorber particles if any, are deposited on a uniformly moving endless screen 8 and are held on the screen by a draft induced by an aspirating mechanism 9. The rate and manner of deposition of the filaments are controlled by the quantity of the filaments in the air and the aspirating conditions under the screen. Aspirating mechanism 9 should maintain a constant aspirating rate so that the current containing fibers and air is not reflected or horizontally deflected from the screen. The aspirated air can, after passing through a cleaning apparatus (not shown) be returned to the stretching area 3.

The sheet material 7 that forms then passes on for compression and consolidation in a heated embossing mechanism 10 having one smooth and one embossed roller.

Two embodiments of the absorbent body according to the invention will now be described by way of example. One of them is provided with a superabsorbing polymer (abbreviated SAP). Both versions are compared with a diaper fluff according to the state of the art as used as an absorbent component in baby diapers.

|  | Absorbent body according to the invention | | Diaper absorbent layer (state of the art) |
|---|---|---|---|
|  | Example 1 | Example 2 |  |
| Composition | 10 wt % endless filaments (polyproylene), rest cellulose fluff | | 100 wt % cellulose fluff |
| *Superabsorber (SAP) | 25 wt % | — | — |
| Specific weight (g/sq m) | 300 | 300 | 500 |
| Thickness (mm) | 1.25 | 1.25 | 6.05 |
| Density (g/cu cm) | 0.24 | 0.24 | 0.083 |
| Max. tensile strength (N/5 cm) |  |  |  |
| dry/lengthwise | 20.6 | 38.9 |  |
| dry/crosswise | 29.4 | 38.6 | not measur- |

-continued

| | Absorbent body according to the invention | | Diaper absorbent layer (state of the art) |
| --- | --- | --- | --- |
| | Example 1 | Example 2 | |
| wet/lengthwise | 6.4 | 14.9 | able |
| wet/crosswise | 10.6 | 9.8 | |
| Maximum elongation (%) | | | |
| dry/lengthwise | 35 | 80 | not measurable |
| dry/crosswise | 34 | 73 | |
| Liq. absorption capacity (g/g) | | | |
| **TBA 30 sec. | 11.4 | 7.9 | 17.2 |
| TBA 600 sec. | 23.5 | 9.3 | 19.1 |
| **TBR 30 sec. | 7.4 | 2.3 | 2.8 |
| TBR 600 sec. | 8.7 | 3.5 | 3.1 |

*Hydrolyzed acrylonitrile grafted starch
**TBA/TBR: Absorption/retention in the "teabag" test.

To determine the absorption and retention in the tea bag test, a precisely weighed amount of sample is welded into a teabag and immersed in the test liquid for given periods of time to soak itself full. It is allowed to drip for 5 minutes and weighed, then centrifuged in a commercial laundry spinner at 1400 rpm, and again weighed.

$$A = \frac{\text{Mass (teabag with sample after dripping} - \text{reference)}}{\text{Dry mass of the sample}}$$

The retention ($R$) is computed as follows:

$$R = \frac{\text{Mass (teabag with sample after spinning} - \text{reference)}}{\text{Dry mass of the sample}}$$

The reference is determined with an empty teabag under the same conditions.

Figure 2:
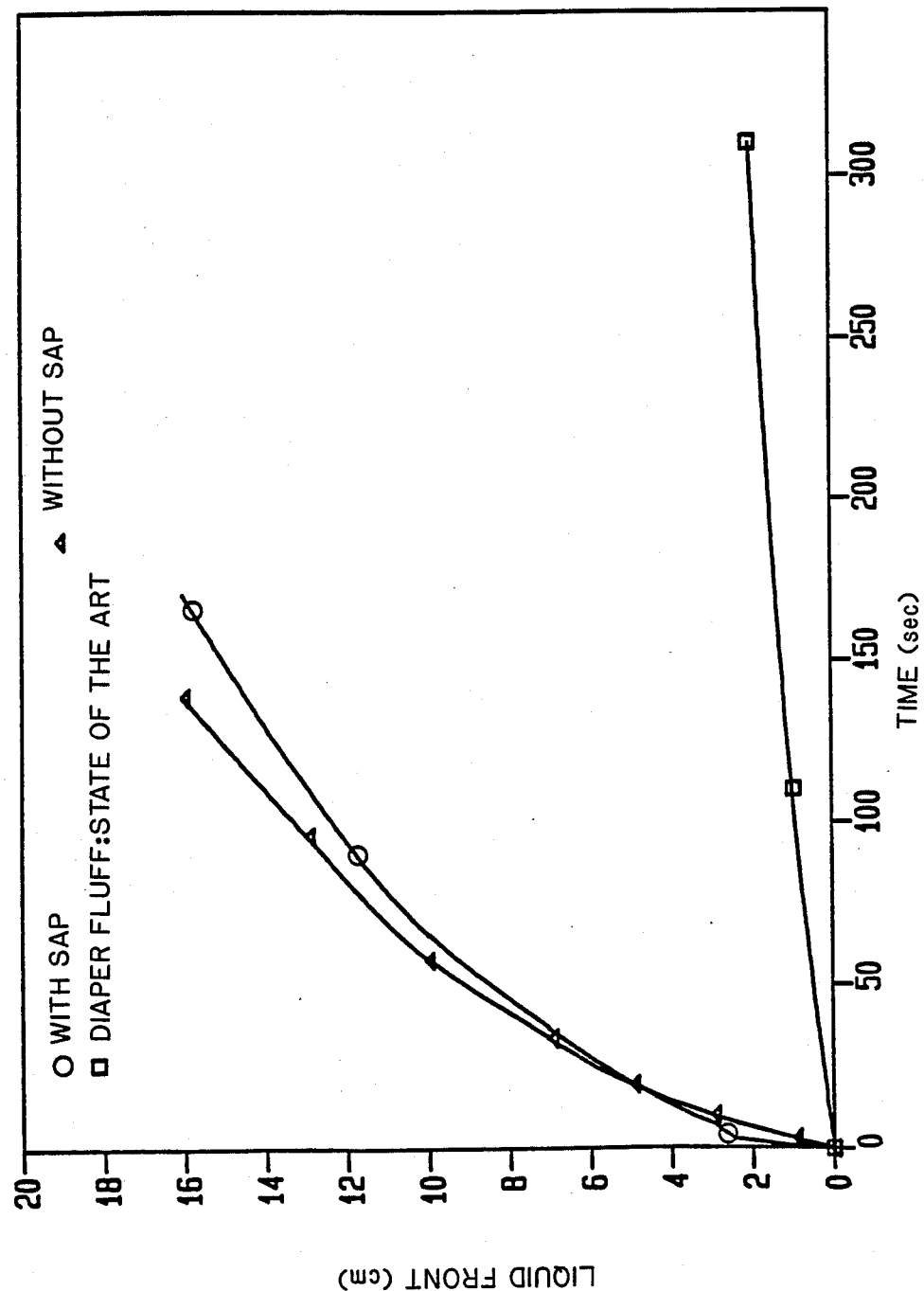
FIG. 2 shows a comparison between diaper fluff and two absorbent bodies of the invention with regard to the ability to transport liquid.

The rate of liquid absorption in the sample is determined by the spreading test (see FIG. 2). In this test the angle of inclination of the absorbent layer can be adjusted between 0° and 60°.

The apparatus for this purpose consists of a trough (8 cm × 25 cm) in the face of which a recess is made. In the latter the sample is dipped in the test liquid during the measurement.

The measurement of the rate of absorption is performed automatically by measuring conductivity. While one electrode is immersed in the test liquid the counter-electrodes are pushed into the absorbent layer.

When the leading edge of the electrically conductive liquid reaches the first needle a definite current flows. As the leading edge advances the current increases by the same amount as each additional needle is reached. The measured current is recorded in relation to time with a recording meter.

The test liquid is synthetic urine consisting of:
19.4 g urea;
8.3 g sodium chloride;
1.0 g magnesium sulfate;
0.6 g calcium chloride; and
970.7 g distilled water.

The absorbent body of Example 1 of the above Table contains superabsorber and, though a very thin product, distributes the liquid very well. FIG. 2 indicates how its absorbent layer shortly swells up and even exceeds the capacity of conventional diaper cellulose (TBA 600 sec.) Also, the retentivity (TBR 600) at 8.7 g/g is substantially better than in the case of the baby diaper. Also very good are the values for the wet and dry strength (Table) which cannot be determined with the absorbent layers from conventional diapers because they have no inherent strength.

The absorbent body of Example 2 contains no superabsorber and therefore has virtually no retentive capacity. As regards strength and ability to distribute liquid, however, it is also far superior to conventional diaper fluff, as it can be seen from the Table and FIG. 2.

It will be understood that the specification and Examples are illustrative but not limitative of the present invention and that other embodiments within the spirit and scope of the invention will suggest themselves to those skilled in the art.

We claim:

1. An absorbent body comprising:
   a nonwoven material of hydrophilic or oleophilic fibers of 1 to 50 mm length in a single-layer network having a total density of 0.05 to 0.5 g/cm$^3$ and a matrix of thermoplastic endless filaments of circular cross section and a high degree of orientation, arranged in a three-dimensional random texture in which the fibers are distributed in a spatially uniform manner in an amount of 40 to 90 wt.-% of the total body.

2. The absorbent body of claim 1 further comprising 2 to 50 weight-percent of a polymeric superabsorber.

3. The absorbent body of claim 2 wherein the super absorber is embedded in a spatially uniform distribution.

4. The absorbent body of claim 3 wherein it is greatly compressed.

5. The absorbent body of claim 4 wherein the thermoplastic filaments are not fused together at their intersections.

6. The absorbent body of claim 3 wherein the superabsorbers adhere to the fibers and filaments.

7. The absorbent body of claim 1 wherein the hydrophilic fibers are selected from the group consisting of cellulose, staple rayon, cotton, linters, mechanical wood pulp or mixtures thereof.

8. The absorbent body of claim 1 wherein the oleophilic fibers consist of polyolefins or oleophilized mechanical wood pulp.

9. A method for production of an absorbent body according to claim 1 comprising:
   spinning in a spinning means one or more rows of filaments from a melt;
   passing the filaments through a stretching zone in a downwardly oriented air stream toward an air permeable support means;
   adding fibers of 1 to 50 mm length in an amount of 40 to 90 wt.-% to the filaments in a mixing zone to contact said fibers with said filaments when said filaments are no longer tacky, said mixing zone being located in a lower third of the distance between the spinning means and said support means;
   depositing the filaments and fibers on said support means;
   controlling the movement of said support means so that the filaments are deposited in a three dimensional, uniform random texture and mixed with said fibers; and
   aspirating air beneath said support means.

10. The method of claim 9 wherein superabsorbent polymeric material is added in an amount of 2 to 50 wt.-% with respect to the total weight of the deposited material with said fibers.

11. The method of claim 9 further comprising:

compressing the deposited filaments and fibers with a line pressure of no more than 150 kp/cm under the action of an amount of moisture that is such that it makes the superabsorbent particle surfaces tacky, but without initiating the swelling process.

12. The method of claim 9 wherein the melt is polypropylene, polyethylene, polyester, polyamide or polyurethane.

13. The method of claim 9 wherein the fibers are hydrophilic.

14. The method of claim 9 wherein the fibers are oleophilic.

* * * * *